US007449449B2

(12) United States Patent
Johnston et al.

(10) Patent No.: US 7,449,449 B2
(45) Date of Patent: Nov. 11, 2008

(54) PARTICLE-MEDIATED TRANSFORMATION OF VERTEBRATE TISSUE CELLS

(75) Inventors: Stephen A. Johnston, Dallas, TX (US); John C. Sanford, Livonia, NY (US)

(73) Assignees: Duke University, Durham, NC (US); Cornell University, Ithaca, NY (US)

( * ) Notice: Subject to any disclaimer, the term of this patent is extended or adjusted under 35 U.S.C. 154(b) by 681 days.

(21) Appl. No.: 10/610,651

(22) Filed: Jul. 2, 2003

(65) Prior Publication Data

US 2004/0097458 A1    May 20, 2004

Related U.S. Application Data

(60) Continuation of application No. 09/755,199, filed on Jan. 8, 2001, now abandoned, which is a continuation of application No. 08/892,351, filed on Jul. 14, 1997, now abandoned, which is a continuation of application No. 08/103,814, filed on Aug. 6, 1993, now abandoned, which is a continuation of application No. 07/864,638, filed on Apr. 7, 1992, now abandoned, which is a division of application No. 07/437,848, filed on Nov. 16, 1989, now abandoned.

(51) Int. Cl.
*A01N 43/04* (2006.01)
*A61K 31/70* (2006.01)
*C12N 15/87* (2006.01)

(52) U.S. Cl. .................. 514/44; 435/320.1; 435/459
(58) Field of Classification Search .................. 514/44; 435/459
See application file for complete search history.

(56) References Cited

U.S. PATENT DOCUMENTS

| | | | |
|---|---|---|---|
| 3,931,397 | A | 1/1976 | Harnden |
| 4,224,404 | A | 9/1980 | Viza et al. |
| 4,394,448 | A | 7/1983 | Szoka, Jr. et al. |
| 4,689,320 | A | 8/1987 | Kaji |
| 4,699,880 | A | 10/1987 | Goldstein |
| 4,704,692 | A | 11/1987 | Ladner |
| 4,738,927 | A | 4/1988 | Taniguchi et al. |
| 4,761,375 | A | 8/1988 | Clark |
| 4,798,786 | A | 1/1989 | Tice et al. |
| 4,806,463 | A | 2/1989 | Goodchild et al. |
| 4,870,009 | A | 9/1989 | Evans et al. |
| 4,944,942 | A | 7/1990 | Brown et al. |
| 4,945,050 | A | 7/1990 | Sanford et al. |
| 5,100,792 | A | 3/1992 | Sanford et al. |
| 5,204,253 | A | 4/1993 | Sanford et al. |
| 5,589,466 | A | 12/1996 | Felgner et al. |
| 5,703,057 | A | 12/1997 | Johnston et al. |
| 6,194,389 | B1 | 2/2001 | Johnston et al. |

FOREIGN PATENT DOCUMENTS

| | | |
|---|---|---|
| EP | 0 270 356 | 6/1988 |
| EP | 0 301 749 | 2/1989 |
| EP | 0 465 529 | 1/1992 |
| FR | 7781 | 3/1970 |
| WO | 86/00930 | 2/1986 |
| WO | 91/00359 | 1/1991 |
| WO | 91/07487 | 5/1991 |
| WO | 95/05853 | 3/1995 |
| WO | 97/19675 | 6/1997 |
| WO | 97/37966 | 10/1997 |

OTHER PUBLICATIONS

S. Akhtar, et al., "*Anti-HIV therapy with antisense oligonucleotides and ribozymes: realistic approaches or expensive myths,*" 38 Journal of Antimicrobial Chemotherapy 159-165 (1996).
M. Böttger, et al., "*Condensation of vector DNA by the chromosomal protein HMG1 results in efficient transfection,*" 950 Biochimica et Biophysica 221-228 (1988).
J. Boynton, et al., "*Chloroplast Transformation in Chamydomonas with High Velocity Microprojectiles,*" 240 Science 1534-1538 (Jun. 10, 1988).
A. Branch, "*A good antisense molecule is hard to find,*" 23 TIBS 45-50 (Feb. 1998).
R. A. F. Clark, "*Overview and General Considerations of Wound Repair,*" The Molecular and Cellular Biology of Wound Repair 3-33 (1998).
S.T. Crooke "*Basic Principles of Antisense Therapeutics,*" 131(12) Handbook of Experimental Pharmacology 1-50 (1997).
J. J. Donnelly, et al., "*DNA Vaccines,*" 15 Annual Review Immunology 617-648 (1997).
M. D. Eisenbraun, et al., "*Examination of Parameters Affecting the Elicitation of Humoral Immune Responses by Particle Bombardment-Mediated Genetic Immunization,*" 12(9) DNA and Cell Biology 791-797 (1993).
P. T. C. Ho, et al., "*Antisense Oligonucleotides as Therapeutics for Malignant Diseases,*" 24(2) Seminars in Oncology 187-202 (Apr. 1997).
J. L. Jainchill, et al., "*Murine Sarcoma and Leukemia Viruses: Assay Using Clonal Lines of Contact-Inhibited Mouse Cells,*" 4(5) Journal of Virology 549-553 (1969).
S. A. Johnston, et al., "*Gene Gun Transfection of Animal Cells and Genetic Immunization,*" 43 Methods in Cell Biology 353-365 (1994).
E. T. Keller, et al., "In vivo *particle-mediated cytokine gene transfer into canine oral mucosa and epidermis,*" 3(3) Cancer Gene Therapy 186-191 (1996).

(Continued)

*Primary Examiner*—Deborah Crouch
(74) *Attorney, Agent, or Firm*—Sharon E. Crane; Bingham McCutchen LLP

(57) ABSTRACT

A method of transferring a gene to vertebrate cells is disclosed. The method comprises the steps of: (a) providing microprojectiles, the microprojectiles carrying polynucleic acid sequences, the sequences comprising, in the 5' to 3' direction, a regulatory sequence operable in the tissue cells and a gene positioned downstream of the regulatory sequence and under the transcriptional control thereof; and (b) accelerating the microprojectiles at the cells, with the microprojectiles contacting the cells at a speed sufficient to penetrate the cells and deposit the polynucleic acid sequences therein. Preferably, the target cells reside in situ in the animal subject when they are transformed. Preferred target cells are dermis or hypodermis cells, and preferred genes for insertion into the target cells are genes which code for proteins or peptides which produce a physiological response in the animal subject.

17 Claims, 4 Drawing Sheets

OTHER PUBLICATIONS

T. M. Klein, et al., "*Factors Influencing Gene Delivery into Zea Mays Cells by High-Velocity Microprojectiles*," 6 Bio/Technology 559-563 (May 1988).

C. M. Nicolet, et al., "*Expression of a tumor-reactive antibody-interleukin 2 fusion protein after* in vivo *particle-mediated gene delivery*," 2(3) Cancer Gene Therapy 161-170 (1995).

L. E. Rosenberg, et al., "*Gene Therapist, Heal Thyself*." 287 Science (Mar. 10, 2000).

J. C. Sanford, "*The biolistic process*," 6 TIBTECH Reviews 299-302 (Dec. 1988).

R. W. Wilfred, et al., "*Counterion-Induced Condensation of Deoxyribonucleic Acid. A Light-Scattering Study*," 18(11) American Chemical Society Biochemistry 2192-2196 (1979).

Beddow Particulate science and technology pp. 3-37, vol. 5, No. 1, 1987.

Journal of Cellular Biochemistry, UCLA Symposia on Molecular & Cellular Biology, Abstracts, 19th Annual Meetings, Jan. 1990, Alan R. Liss, Inc.

Transcript of speech entitled "Particle Propulsion by electric Discharge at the AAAS Meeting on Plant Molecular Biology/Genetic Engineering for Agriculture (VI)", Jan. 1989, by Winston Brill. Tape available from AAAS.

G. Acsadi et al., "Direct Gene Transfer and Expression into Rat Heart in Vivo", The New Biologist, Jan. 1991, pp. 71-81, vol. 3, No. 1.

W.F. Anderson, "Gene Therapy—Several hundred patients have already received treatment. In the next century the procedure will be commonplace", Scientific American, Sep. 1995, pp. 124-128, Scientific American Inc., New York, NY.

P. Anker et al., "The Role of Extracellular DNA in the Transfer of Information From T to B Human Lymphocytes in the Course of an Immune Response", J. Immunogenet., 1980, pp. 475-481, vol. 7, Blackwell Scientific Publications.

P. Anker et al., "Nude Mice Injected with DNA Excreted by Antigen-Stimulated Human T Lymphocytes Synthesize Specific Human Antibodies", Expl. Cell. Biol., 1984, pp. 133-136, vol. 52, Karger, Basel.

P. Anker et al., "Transfert d'information de lymphocytes T à B au cours d'une réponse immune: rôle de l'ADN extracellulaire", Schweiz. Med. Wschr., 1980, pp. 1444-1446, vol. 110.

P. Anker et al., "Spontaneous Release of DNA by Human Blood Lymphocytes as Shown in an in Vitro System", Cancer Res., Sep. 1975, pp. 2375-2382, vol. 35.

K. Anwer et al., "Synergistic Effect of Formulated Plasmid and Needle-Free Injection for Genetic Vaccines", Pharm. Res., 1999, pp. 889-895, vol. 16, No. 6, Plenum Publishing Corporation.

J.D. Appel et al., "Asbestos fibers mediate transformation of monkey cells by exogenous plasmid DNA", Proc. Natl. Acad. Sci USA, 1988, pp. 7670-7674, vol. 85, The National Academy of Sciences, Washington, DC.

R. Aubin et al., "Polybrene/DMSO-Assisted Gene Transfer", Methods in Molecular Biology, 1991, pp. 35-43, vol. 7, Chapter 4, The Humana Press Inc., Clifton, NJ.

W. Bains, "Anti-idiotype Antibodies", Biotechnology From A to Z (2d ed.), 1988, pp. 17-19, Oxford University Press.

Baker et al., "The Study of Biology: The Fourth Edition", 1982, pp. 145-150, Addison-Wesley Publishing Company.

J.A. Bellanti, "Theories of Antibody Formation", Immunology III, 1985, pp. 154-155, W.B. Saunders Company.

N. Benvenisty et al., "Direct introduction of genes into rats and expression of the genes", Proc. Natl. Acad. Sci. USA, Dec. 1986, pp. 9551-9555, vol. 83, The National Academy of Sciences, Washington, DC.

H.M. Blau et al., "Molecular Medicine—Gene Therapy—A Novel Form of Drug Delivery", The New England J. Med., Nov. 2, 1995, pp. 1204-1207, vol. 333, No. 18, Massachusetts Medical Society.

O.F. Borisova et al., "Secondary structure of nuclear precursors of the informational RNA (pre-mRNA)", Mol. Biol. (Mosk), Sep.-Oct. 1976, pp. 1094-1102, vol. 10, No. 5.

L. Bouchard et al., "Tumorigenic Activity of Polyoma Virus and SV40 DNAs in Newborn Rodents", Virology, 1984, pp. 53-64, vol. 135, Academic Press, Inc.

O. Boussif et al., "A versatile vector for gene and oligonucleotide transfer into cells in culture and in vivo: Polyethylenimine", Proc. Natl. Acad. Sci. USA, Aug. 1995, pp. 7297-7301, vol. 92, The National Academy of Sciences, Washington, DC.

J.E. Boynton et al., "Chloroplast Transformation in *Chlamydomonas* with High Velocity Microprojectiles", Science, 1988, p. 1534, vol. 240, American Association for the Advancement of Science, Washington, DC.

H.W. Chan et al., "Molecular Cloning of Polyoma Virus DNA in *Escherichia coli*: Lambda Phage Vector System", Science, Mar. 1979, pp. 887-892, vol. 203, American Association for the Advancement of Science, Washington, DC.

S.C. Chen et al., "Protective Immunity Induced by Oral Immunization With a Rotavirus DNA Vaccine Encapsulated in Microparticles", Journal of Virology, Jul. 1998, pp. 5757-5761, vol. 72, No. 7, ASM Press, Washington, DC.

O. Chisholm et al., "Transfection of myeloid cell lines using polybrene/DMSO", Nucleic Acids Research, 1988, p. 2352, vol. 16, Nol. 5, IRL Press Limited, Oxford, England.

P. Christou et al., "Stable Transformation of Soybean Callus by DNA-Coated Gold Particles," Plant Physiol., 1988, pp. 671-674, vol. 87, No. 3, American Society of Plant Physiologists.

J. Cohen, "Research News: Naked DNA Points Way to Vaccines", Science, Mar. 19, 1993, pp. 1691-1692, vol. 259, American Association for the Advancement of Science, Washington, DC.

L. Coney et al., "Facilitated DNA inoculation induces anti-HIV-1 immunity in vivo", Vaccine, 1994, pp. 1545-1550, vol. 12, No. 16, Butterworth-Heinemann Ltd.

R.M. Conry et al., "Characterization of a Messenger RNA Polynucleotide Vaccine Vector", Cancer Research, Apr. 1995, pp. 1397-1400, vol. 55.

M. Danielsen et al., "The mouse glucocorticoid receptor: mapping of functional domains by cloning, sequencing and expression of wild-type and mutant receptor proteins", The EMBO Journal, 1986, pp. 2513-2522, vol. 5, No. 10, IRL Press Limited, Oxford England.

J. Davey et al., "Location of Influenza Virus M, NP and NS1 Proteins in Microinjected Cells", J. Gen. Virol., 1985, pp. 2319-2334, vol. 66, Society of General Microbiology, Great Britain.

H.L. Davis et al., "Use of Plasmid DNA for Direct Gene Transfer and Immunization", Annals New York Academy of Sciences, pp. 21-29, 1995.

S.J. De Souza et al., "Collagen Binding Site in Collagenase Can Be Determined Using the Concept of Sense-Antisense Peptide Interactions", J. Biol. Chem., 1992, pp. 13763-13767, vol. 267, No. 19, The American Society for Biochemistry and Molecular Biology, Inc.

J. R. De Wet et al., "Firefly Luciferase Gene: Structure and Expression in Mammalian Cells", Molecular and Cellular Biology, Feb. 1987, pp. 725-737, vol. 7, No. 2, ASM Press, Washington, D.C.

S.C. De Smedt et al., "Cationic Polymer Based Gene Delivery Systems", Pharm. Res., 2000, pp. 113-126, vol. 17, No. 2, Plenum Publishing Corporation.

R.R. Deck et al., "Characterization of humoral immune responses induced by an influenza hemagglutinin DNA vaccine", Vaccine, 1997, pp. 71-78, vol. 15, No. 1, Elsevier Science Ltd, Great Britain.

F.M. Denoto et al., "Human growth hormone DNA sequence and mRNA structure: possibe alternative splicing", Nucl. Acids Res., 1981, pp. 3719-3730, vol. 9, No. 15, IRL Press Limited, United Kingdom.

R.J. Desnick et al., "Gene therapy for genetic diseases", Acta Paediatrica Japonica, 1998, pp. 191-203, vol. 40.

B. Dixon, "Commentary" The Third Vaccine Revolution, Biotechnology, 1995, p. 420, vol. 13.

J.J. Donnelly et al., "Preclinical efficacy of a prototype DNA vaccine: Enhanced protection against antigenic drift in influenza virus", Nature Medicine, 1995, pp. 583-587, vol. 1, No. 6.

T.W. Dubensky et al., "Direct transfection of viral and plasmid DNA into the liver or spleen of mice", Proc. Natl. Acad. Sci. USA, Dec. 1984, pp. 7529-7533, vol. 81, The National Academy of Sciences, Washington, DC.

J.G. Duguid et al., "A Physicochemical Approach for Predicting the Effectiveness of Peptide-Based Gene Delivery Systems for Use in Plasmid-Based Gene Therapy", Biophys. J., Jun. 1998, pp. 2802-2814, vol. 74, the Biophysical Society.

E. Esposito et al., "Preparation and characterization of cationic microspheres for gene delivery", Int. J . Pharm., 1999, pp. 29-41, vol. 189, Elsevier Science B.V., The Netherlands.

I. Fainboim et al., "Transfer of experimental allergic orchitis with immune RNA, Studies in vivo", Clin. Exp. Immunol., 1978, pp. 92-99, vol. 34, Blackwell Scientific Publications.

F.E. Farber et al., "Optimal Conditions for Uptake of Exogenous DNA by Chinese Hamster Lung Cells Deficient in Hyposanthine-guanine Phosphoribosyltransferase", Biochimica et Biophysica Acta, 1975, pp. 298-311, vol. 390, Elsevier Scientific Publishing Company, The Netherlands.

M.A. Feitelson et al., "A Chronic Carrierlike State is Established in Nude Mice injected with Cloned Hepatitis B Virus DNA", J. Virol., Apr. 1988, pp. 1408-1415, vol. 62, No. 4, ASM Press, Washington, DC.

P. Felgner et al., "Lipofection: A highly efficient, lipid-mediated DNA-transfection procedure", Proc. Natl. Acad. Sci. USA, Nov. 1987, pp. 7413-7417, vol. 84, The National Academy of Sciences, Washington, DC.

B.N. Fields et al., Fields Virology, 1990, p. 1680, vol. 2, Chapter 60, Raven Press, NY, NY.

B.N. Fields et al., Virology (2d ed.), 1990, pp. 1596, 1612-1614, Chapter 56, Raven Press, NY.

B. Fields et al., Fields Virology, 1996, p. 2699, vol. 2, Lippincott-Raven Publishers, Philadelphia, PA.

B. Fields et al., Fields Virology, 1996, pp. 46-47, vol. 1, Lippincott-Raven Publishers, Philadelphia, PA.

B.N. Fields et al., "Polyomavirinae and Their Replication", Fields Virology, 1990, p. 1597, vol. 2, Raven Press, NY, NY.

Y.-K. T. Fung et al., "Tumor induction by direct injection of cloned v-src DNA into chickens", Proc. Natl. Acad. Sci. USA, Jan. 1983, pp. 353-357, vol. 80, The National Academy of Sciences, Washington, DC.

E. Fynan et al., "DNA vaccines: Protective Immunizations by Parenternal, Mucosal, and Gene-Gun Inoculations", Proc. Natl. Acad. Sci. USA, Dec. 1993, pp. 11478-11482, vol. 90, The National Academy of Sciences, Washington, DC.

V.S. Gaitskhoki, "Molecular organization of eukaryotic informational RNA", Mol. Biol. (Mosk), Jul.-Aug. 1979, pp. 725-751, vol. 13, No. 4.

M.C. Garnett, "Gene-Delivery Systems Using Cationic Polymers", Crit. Rev. Ther. Drug Carr. Sys., 1999, pp. 147-207, vol. 16, No. 2, Begell House, Inc.

C. Gélinas et al., "Tumorigenic activity of cloned polyoma virus DNA in newborn rats", Experienta, 1981, pp. 1074-1075, vol. 37, Birkhäuser Verlag, Basel, Germany.

C.K. Goldman et al., "In vitro and in vivo gene delivery mediated by a synthetic polycationic amino polymer", Nature Biotech., May 1997, pp. 462-466, vol. 15.

C.M. Gorman et al., "Recombinant Genomes Which Express Chloramphenicol Acetyltransferase in Mammalian Cells", Mol. Cell Biol., Sep. 1982, pp. 1044-1051, vol. 2, No. 9, ASM Press, Washington, DC.

C.M. Gorman et al., "The Rous sarcoma virus long terminal repeat is a strong promoter when introduced into a variety of eukaryotic cells by DNA-mediated transfection", Proc. Natl. Acad. Sci. USA, Nov. 1982, pp. 6777-6781, vol. 79, The National Academy of Sciences, Washington, DC.

F.L. Graham et al., "A New Technique for the Assay of Infectivity of Human Adenovirus 5 DNA", Virology, 1973, pp. 456-467, vol. 52, Academic Press, Inc.

R. Gramzinski et al., "Immune Response to Hepatitis B DNA Vaccine in Aotus Monkeys: A Comparison of Vaccine Formulation, Route, and Method of Administration", Molecular Medicine, Feb. 1998, pp. 109-118, vol. 4, No. 2, The Picower Institute Press.

R. Gramzinski et al., "Optimization of Antibody Responses of a Malaria DNA Vaccine in Aotus Monkeys", Vaccine Research, 1996, pp. 173-183, vol. 5, No. 3, Mary Ann Liebert, Inc.

N. Hanania et al., "Isolation of a mouse DNA fraction which encodes more informational than non information RNA sequences", Mol. Biol. Rep., Mar. 1982, pp. 91-96, vol. 8, No. 2.

M.A. Israel et al., "Molecular Cloning of Polyoma Virus DNA in Escherichia coli: Plasmid Vector System", Science, Mar. 1979, pp. 883-887, vol. 203, American Association for the Advancement of Science, Washington, DC.

M.A. Israel et al., "Biological Activity of Polyoma Viral DNA in Mice and Hamsters", J. Virol., Mar. 1979, pp. 990-996, vol. 29, No. 3.

D. Jacherts et al., "Antibody Response in Rhesus Monkeys and Guinea Pigs to Inoculation With RNA Derived From Antigenically Stimulated Cell-Free Systems", J. Immunol., 1970, pp. 746-752, vol. 104, The William & Wilkins Co.

D. Jachertz et al., "Information carried by the DNA released by antigen-stimulated lymphocytes", Immunology, 1979, pp. 753-763, vol. 37, Blackwell Scientific Publications.

D. Jachertz et al., "Treatment of P815 Mastocytoma in DBA/2 Mice With RNA", J. Immunogen., 1974, pp. 355-362, vol. 1.

S. Jiao et al., "Direct Gene Transfer into Nonhuman Primate Myofibers In Vivo", Human Gene Therapy, 1992, pp. 21-33, vol. 3, Mary Ann Liebert, Inc.

S. Johnston et al., "Mitochondrial Transformation in Yeast by Bombardment with Microprojectiles", Science, 1988, p. 1538, vol. 240, American Association for the Advancement of Science, Washington, DC.

D.H. Jones et al., "Poly(DL-lactide-co-glycolide)-encapsulated plasmid DNA elicits systemic and mucosal antibody responses to encoded protein after oral administration", Vaccine, 1997, pp. 814-817, vol. 15, No. 8, Elsevier Science Ltd., Great Britain.

S. Kawai et al., "New Procedure for DNA Transfection with Polycation and Dimethyl Sulfoxide", Molecular and Cellular Biology, Jun. 1984, pp. 1172-1174, vol. 4, No. 6, ASM Press, Washington, DC.

A. Kichler et al., "Efficient DNA Transfection Mediated by the C-Terminal Domain of Human Immunodeficiency Virus Type 1 Viral Protein R", J. Virol., Jun. 2000, pp. 5424-5431, vol. 74, No. 12, ASM Press, Washington, DC.

R. Kircheis et al., "Polycation-Based DNA Complexes for Tumor-Targeted Gene Delivery in vivo", J. Gene Med., 1999, pp. 111-120, vol. 1, John Wiley & Sons, Ltd.

T.M. Klein et al., "High-velocity microprojectiles for delivering nucleic acids into living cells", Nature, May 1987, pp. 70-73, vol. 327, No. 6117, Macmillan Publishers.

T.M. Klein et al., "Transfer of foreign genes into intact maize cells with high-velocity microprojectiles", Proc. Natl. Acad. Sci. USA, Jun. 1988, pp. 4305-4309, vol. 85, No. 12, The National Academy of Sciences, Washington, DC.

D.M. Klinman, et al., "Contribution of CpG Motifs to the Immunogenicity of DNA Vaccines", J. Immunol., 1997, pp. 3635-3639, vol. 158, The American Association of Immunologists.

M. Koenig et al., "The Complete Sequence of Dystrophin Predicts a Rod-Shaped Cytoskeletal Protein", Cell, 1988, pp. 219-228, vol. 53, No. 2, Cell Press.

T.V. Koloskova et al., "Genetic diversity of informational RNA in rat tissues", Biokhimiia, Feb. 1982, pp. 305-311, vol. 47, No. 2.

A.M. Krieg et al., "Sequence motifs in adenoviral DNA block immune activation by stimulatory CpG motifs", Proc. Natl. Acad. Sci. USA, 1998, pp. 12631-12636, vol. 95, The National Academy of Sciences, Washington, DC.

Krieg et al., Proc. Natl. Acad. Sci. USA, 1998, pp. 12631-12636, vol. 95, The National Academy of Sciences, Washington, DC.

I. Kruczek et al., "Expression of the chloramphenicol acetyltransferase gene in mammalian cells under the control of adenovirus type 12 promoters: Effect of promoter methylation on gene expression", Proc. Natl. Acad. Sci USA, Dec. 1983, pp. 7586-7590, vol. 80, The National Academy of Sciences, Washington, DC.

N. Kuklin et al., "Induction of Mucosal Immunity Against Herpes Simplex Virus by Plasmid DNA Immunization", Journal of Virology, Apr. 1997, pp. 3138-3145, vol. 71, No. 4, ASM Press, Washington, DC.

J.F. Kukowska-Latallo et al., Proc. Natl. Acad. Sci. USA, 1996, pp. 4897-4902, vol. 93, The National Academy of Sciences, Washington, DC.

R. A. Lake et al., "Transfection of the Chloramphenicol-Acetyltransferase Gene into Eukaryotic Cells Using Diethyl- Aminoethyl (DEAE)-Dextran", Methods in Molecular Biology, 1991, pp. 23-33, vol. 7, Chapter 3, The Humana Press Inc., Clifton, NJ.

O. Laub et al., "Synthesis of Hepatitis B Surface Antigen in Mammalian Cells: Expression of the Entire Gene and the Coding Region", J. Virol., Oct. 1983, pp. 271-280, vol. 48, No. 1, ASM Press, Washington, DC.

P. Lemieux et al., "A combination of poloxamers increases gene expression of plasmid DNA in skeletal muscle", Gene Therapy, 2000, pp. 986-991, vol. 7.

J.-M. Li et al., "Efficient Gene Delivery to Vascular Smooth Muscle Cells Using a Nontoxic, Synthetic Peptide Vector System Targeted to Membrane Integrins: A First Step Toward the Gene Therapy of Chronic Rejection", Transplantation Proceedings, 2001, p. 589, vol. 33, Elsevier Science Inc., NY.

J. Liaw et al., "In vivo gene delivery into ocular tissues by eye drops of poly(ethylene oxide)-poly(propylene oxide)-poly(ethylene oxide) (PEO-PPO-PEO) polymeric micelles", Gene Therapy, 2001, pp. 999-1004, vol. 8.

OPTI-MEM I Reduced Serum Medium modification of MEM (Eagle's), Apr. 1999, Life Technologies.

H. Lin et al., "Expression of Recombinant Genes in Myocardium In Vivo After Direct Injection of DNA", Circulation, Dec. 1990, pp. 2217-2221, vol. 82, No. 6.

S. Liptay et al., "Colon Epithelium Can Be Transiently Transfected with Liposomes, Calcium Phosphate Precipitation and DEAE Dextran in vivo", Digestion, 1998, pp. 142-147, vol. 59, S. Karger AG, Basel, Germany.

D.M. Livingston et al., "Replication of Papovaviruses", Virology, 1985, pp. 393-3410, Raven Press, NY, NY.

M.A. Lopata et al., "High level transient expression of a chloramphenicol acetyl transferase gene by DEAE-dextran mediated DNA transfection coupled with a dimethyl sulfoxide or glycerol shock treatment", Nucleic Acids Res., 1984, pp. 5707-5717, vol. 12, No. 14, IRL Press Limited, Oxford, England.

D. Luo et al., "Controlled DNA Delivery Systems", Pharm. Res., 1999, pp. 1300-1308, vol. 16, No. 8, Plenum Publishing Corporation.

D. Luo et al., "Synthetic DNA delivery systems", Nature Biotechnology, Jan. 2000, pp. 33-37, vol. 18, Nature America Inc.

F.C. Maclaughlin et al., "Chitosan and depolymerized chitosan oligomers as condensing carriers for in vivo plasmid delivery", Journal of Controlled Release, 1998, pp. 259-272, vol. 56, Elsevier Science B.V., The Netherlands.

C.W. Mandl et al., "In vitro-synthesized infectious RNA as an attenuated live vaccine in flavivirus model", Nature Medicine, Dec. 1998, pp. 1438-1440, vol. 4, No. 12.

M. Manthorpe et al., "Gene Therapy by Intramuscular Injectin of Plasmid DNA: Studies on Firefly Luciferase Gene Expression in Mice", Human Gene Therapy, 1993, pp. 419-431, vol. 4, Mary Ann Liebert, Inc.

H.-Q. Mao et al., "Chitosan-DNA nanoparticles as gene carriers: synthesis, characterization and transfection efficiency", Journal of Controlled Release, 2001, pp. 399-421, vol. 70, Elsevier Science B.V., The Netherlands.

E. Marshall, "Gene Therapy's Growing Pains", Science News Report, Science, 1995, pp. 1050-1055, vol. 269, American Association for the Advancement of Science, Washington, DC.

T. Martin et al., "Plasmid DNA Malaria Vaccine: The Potential for Genomic Integration after Intramuscular Injection", Human Gene Therapy, Mar. 1999, pp. 759-768, vol. 10, Mary Ann Liebert, Inc.

D.E. McCabe et al., "Stable Transformation of Soybean (*Glycine Max*) by Particle Acceleration", Bio/Technology, Aug. 1988, pp. 923-926, vol. 6, Nature Publishing Company.

R.J. Mumper et al., "Protective interactive noncondensing (PINC) polymers for enhanced plasmid distribution and expression in rat skeletal muscle", Journal of Controlled Release, 1998, pp. 191-203, vol. 52, Elsevier Science B.V., The Netherlands.

R.J. Mumper et al., "Polyvinyl Derivatives as Novel Interactive Polymers for Controlled Gene Delivery to Muscle", Pharmaceutical Research, 1996, pp. 701-709, vol. 13, No. 5, Plenum Publishing Corp.

C. Nicolau et al., "In vivo expression of rat insulin after intravenous administration of the liposome-entrapped gene for rat insulin I", Proc. Natl. Acad. Sci. USA, Feb. 1983, pp. 1068-1072, vol. 80, The National Academy of Sciences, Washington, DC.

C. Nicolau et al., "Liposomes as Carriers for in vivo Gene Transfer and Expression", Methods in Enzymology, 1987, pp. 157-176, vol. 149, Academic Press, Inc.

N. Oudrhiri et al., "Gene transfer by guanidinium-cholesterol cationic lipids into airway epithelial cells in vitro and in vivo", Proc. Natl. Acad. Sci. USA, Mar. 1997, pp. 1651-1656, vol. 94, the National Academy of Sciences, Washington, DC.

C.J. Pachuk et al., "Characterization of a new class of DNA delivery complexes formed by the local anesthetic bupivacaine", Biochimica et Biophysica Acta, 2000, pp. 20-30, vol. 1468, Elsevier Science B.V., The Netherlands.

S.J. Pilistine et al., "Placental lactogen administration reverses the effect of low-protein diet on maternal and fetal serum somatomedin levels in the pregnant rat", Proc. Natl. Acad. Sci. USA, Sep. 1984, pp. 5853-5857, vol. 81, the National Academy of Sciences, Washington, DC.

L. Prevec et al., "Use of Human Adenovirus-based Vectors for Antigen Expression in Animals", J. Gen. Virol., 1989, pp. 429-434, vol. 70, Society of General Microbiology, Great Britain.

"IV. Transfection of Eukaryotic Cells With the ProFection™ Systems", Promega Protocols and Applications Guide, Second Edition, Mar. 1991, pp. 297-305, Promega Corporation.

P. Qiu et al., "Gene gun delivery of mRNA in situ results in efficient transgene expression and genetic immunization", Gene Therapy, 1996, pp. 262-268, vol. 3.

S.A. Rosenberg et al., "Biological Activity of Recombinant Human Interleukin-2 Produced in *Escherichia coli*", Science, 1984, pp. 1412-1415, vol. 223, American Association for the Advancement of Science, Washington, DC.

K. Roy et al., "Oral gene delivery with chitosan-DNA nanoparticles generates immunologic protection in a murine model of peanut allergy", Nature Medicine, 1999, pp. 387-391, vol. 5, No. 4.

J. Sambrook et al., "Introduction of Recombinant Vectors into Mammalian Cells", Molecular Cloning, 1989, pp. 16.30-16.81, Cold Spring Harbor Laboratory Press.

J. Sanford et al., "Delivery of substances into cells and tissues using a particle bombardment process", Particulate Science and Technology, 1987, pp. 27-37, vol. 5, Hemisphere Publishing Corp.

Y. Sato et al., "Immunostimulatory DNA Sequences Necessary for Effective Intradermal Gene Immunization", Science, 1996, pp. 352-354, vol. 273, American Association for the Advancement of Science, Washington, DC.

M.L. Satz et al., "Mechanism of immune transfer by RNA extracts", Mol. Cell. Bioch., 1980, pp. 105-113, vol. 33, Dr. W. Junk b.v. Publishers, The Netherlands.

Seeger et al., Proc. Natl. Acad. Sci. USA, 1984, pp. 5849-5852, vol. 81, The National Academy of Sciences, Washington, DC.

S. Sell et al., "Transfer of Specific Immunity With RNA", Arch. Pathol. Lab. Med., May 1978, pp. 217-222, vol. 102.

M.B. Soares et al., "RNA-Mediated Gene Duplication: the Rat Preproinsulin I Gene is a Functional Retroposon", Mol. Cell. Biol., Aug. 1985, pp. 2090-2103, vol. 5, No. 8, ASM Press, Washington, DC.

K. Sokoll, "Polymer Based Formulations", Dec. 2000, pp. 51-60.

C.J.A. Sol et al., "Oncogenicity of SV40 DNA in the Syrian Hamster", J. Gen. Virol., 1977, pp. 635-638, vol. 37, Great Britain.

L.M. Sompayrac, et al., "Efficient infection of monkey cells with DNA of simian virus 40", Proc. Natl. Acad. Sci. USA, Dec. 1981, pp. 7575-7578, vol. 78, No. 12, The National Academy of Sciences, Washington, DC.

St. Louis et al., "An alternative approach to somatic cell gene therapy", Proc. Natl. Acad. Sci. USA, May 1988, pp. 3150-3154, vol. 85, The National Academy of Sciences, Washington, DC.

L. Stryer, Biochemistry, 1981, p. 597, Chapter 25, W.H. Freeman and Company.

C. Sureau et al., "Cloned Hepatitis Delta Virus cDNA is Infectious in the Chimpanzee", Journal of Virology, Oct. 1989, pp. 4292-4297, vol. 63, No. 10, ASM Press, Washington, DC.

D.J. Sussman et al., "Short-Term, High-Efficiency Expression of Transfected DNA", Molecular and Cellular Biology, Aug. 1984, pp. 1641-1643, vol. 4, No. 8, ASM Press, Washington, DC.

D. Tang et al., "Genetic immunization is simple method for eliciting an immune response", Nature, Mar. 1992, pp. 152-154, vol. 356, Nature Publishing Group.

T. Taniguchi et al., "Structure and expression of a cloned cDNA for human interleukin-2", Nature, Mar. 1983, pp. 305-310, vol. 302, Macmillan Journals Ltd.

J. Taylor et al., "Recombinant fowlpox virus inducing protective immunity in non-avian species", Vaccine, Dec. 1988, pp. 497-503, vol. 6, Butterworth & Co. Ltd.

C. Transy et al., "Analysis of Integrated Ground Squirrel Hepatitis Virus and Flanking Host DNA in Two Hepatocellular Carcinomas", Journal of Virology, Aug. 1994, pp. 5291-5295, ASM Press, Washington, DC.

M.R. Venneman et al., "Immunogenicity of Ribonucleic Acid Preparations Obtained from *Salmonella typhimurium*", Infection and Immunity, Jun. 1970, pp. 574-582, vol. 1, No. 6, ASM Press, Washington DC.

I.M. Verma et al., "Gene therapy—promises, problems and prospects", Nature, Sep. 1997, pp. 239-242, vol. 389.

D. Wang et al., "Encapsulation of plasmid DNA in biodegradable poly(D, L-lactic-co-glycolic acid) microspheres as a novel approach for immunogene delivery", Journal of Controlled Release, 1999, pp. 9-18, vol. 57, Elsevier Science B.V., The Netherlands.

C-Y. Wang et al., "pH-sensitive immunoliposomes mediate target-cell-specific delivery and controlled expression of a foreign gene in mouse", Proc. Natl. Acad. Sci. USA, Nov. 1987, pp. 7851-7855, vol. 84, The National Academy of Sciences, Washington, DC.

R. Wang et al., "Induction of Antigen-Specific Cytotoxic T Lymphocytes in Humans by a Malaria DNA Vaccine", Science, Oct. 1998, pp. 476-480, vol. 282, American Association for the Advancement of Science, Washington, DC.

R. Weeratna et al., "Reduction of Antigen Expression from DNA Vaccines by Coadministered Oligodeoxynucleotides", Antisense & Nucl. Acid Drug Devel., 1998, pp. 351-356, vol. 8, Mary Ann Liebert, Inc.

H. Will et al., "Infectious hepatitis B virus from cloned DNA of known nucleotide sequence", Proc. Natl. Acad. Sci. USA, Feb. 1985, pp. 891-895, vol. 82, The National Academy of Sciences, Washington, DC.

H. Will et al., "Cloned HBV DNA causes hepatitis in chimpanzees", Nature, Oct. 1982, pp. 740-742, vol. 299, Macmillan Journals Ltd.

R.S. Williams et al., "Introduction of foreign genes into tissues of living mice by DNA-coated microprojectiles", Proc. Natl. Acad. Sci. USA, Apr. 1991, pp. 2726-2730, vol. 88, The National Academy of Sciences, Washington, DC.

J.A. Wolff et al., "Direct Gene Transfer into Mouse Muscle in vivo", Science, Mar. 1990, pp. 1465-1468, vol. 247, American Association for the Advancement of Science, Washington, DC.

J. A. Wolff et al., "Expression of naked plasmids by cultured myotubes and entry of plasmids into T tubules and caveolae of mammalian skeletal muscle", Journal of Cell Science, 1992, pp. 1249-1259, vol. 103, The Company of Biologists Limited, Great Britain.

J.A. Wolff et al., UCLA Symposia on Mol. Cell. Biol., Abstract D434, Jan. 22-28, 1990, Wiley-Liss.

J.S. Wolff et al., "Conditions Affecting Direct Gene Transfer Into Rodent Muscle In Vivo", BioTechniques, 1991, pp. 474-485, vol. 11, No. 4.

M.J. Wright et al., "In vivo myocardial gene transfer: Optimization, evaluation and direct comparison of gene transfer vectors", Basic Res. Cardiol., 2001, pp. 227-236, vol. 96, No. 3, Steinkopff Verlag.

G.Y. Wu et al., "Receptor-mediated Gene Delivery and Expression in Vivo", J. Biol. Chem., 1988, pp. 14621-14624, vol. 263, No. 29, The American Society for Biochemistry and Molecular Biology, Inc.

A. Wynshaw-Boris et al., "Identification of a cAMP Regulatory Region in the Gene for Rat Cytosolic Phosphoenolpyruvate Carboxykinase (GTP)", J. Biol. Chem., Oct. 1984, pp. 12161-12169, vol. 259, No. 19, The American Society of Biological Chemists, Inc.

L.A. Yakubov et al., "Mechanism of oligonucleotide uptake by cells: Involvement of specific receptors?", Proc. Natl. Acad. Sci. USA, Sep. 1989, pp. 6454-6458, vol. 86, The National Academy of Sciences, Washington, DC.

N-S. Yang, "Gene Transfer into Mammalian Somatic Cells In Vivo", Critical Reviews in Biotechnology, 1992, pp. 335-356, vol. 12, No. 4, CRC Press, Inc.

A.S. Youmans et al., "Factors Affecting Immunogenic Activity of Mycobacterial Ribosomal and Ribonucleic Acid Preparations", Journal of Bacteriology, 1969, pp. 42-50, vol. 99, No. 1, ASM Press, Washington, DC.

A.V. Zelenin et al., "Genetic transformation of mouse cultured cells with the help of high-velocity mechanical DNA injection", FEBS, Feb. 1989, pp. 65-67, vol. 244, No. 1, Elsevier Science Publishers B.V., The Netherlands.

A. Zelenin et al., "Genetic Transformation of Mouse Cultured Cells with the Help of High-Velocity Mechanical DNA Injection", FEBS Letters, 1989, p. 165, vol. 244, No. 1.

X. Zhou et al., "Self-replicating Semliki Forest virus RNA as recombinant vaccine", Vaccine, 1994, pp. 1510-1514, vol. 12, No. 16, Butterworth-Heinemann Ltd.

Baker et al., "The Study of Biology: The Fourth Edition," 1982, pp. 145-150, Addison-Wesley Publishing Company.

Transcript of speech entitled, "Particle Propulsion by electric Discharge at the AAAS Meeting on Plant Molecular Biology/Benetic Engineering for Agriculture (VI)," Jan. 1989, by Winston Brill. Tape available from AAAS.

Letter from Keystone Symp. to Transgene dated Jan. 8, 1999.

DAYS POST-BOMBARDMENT

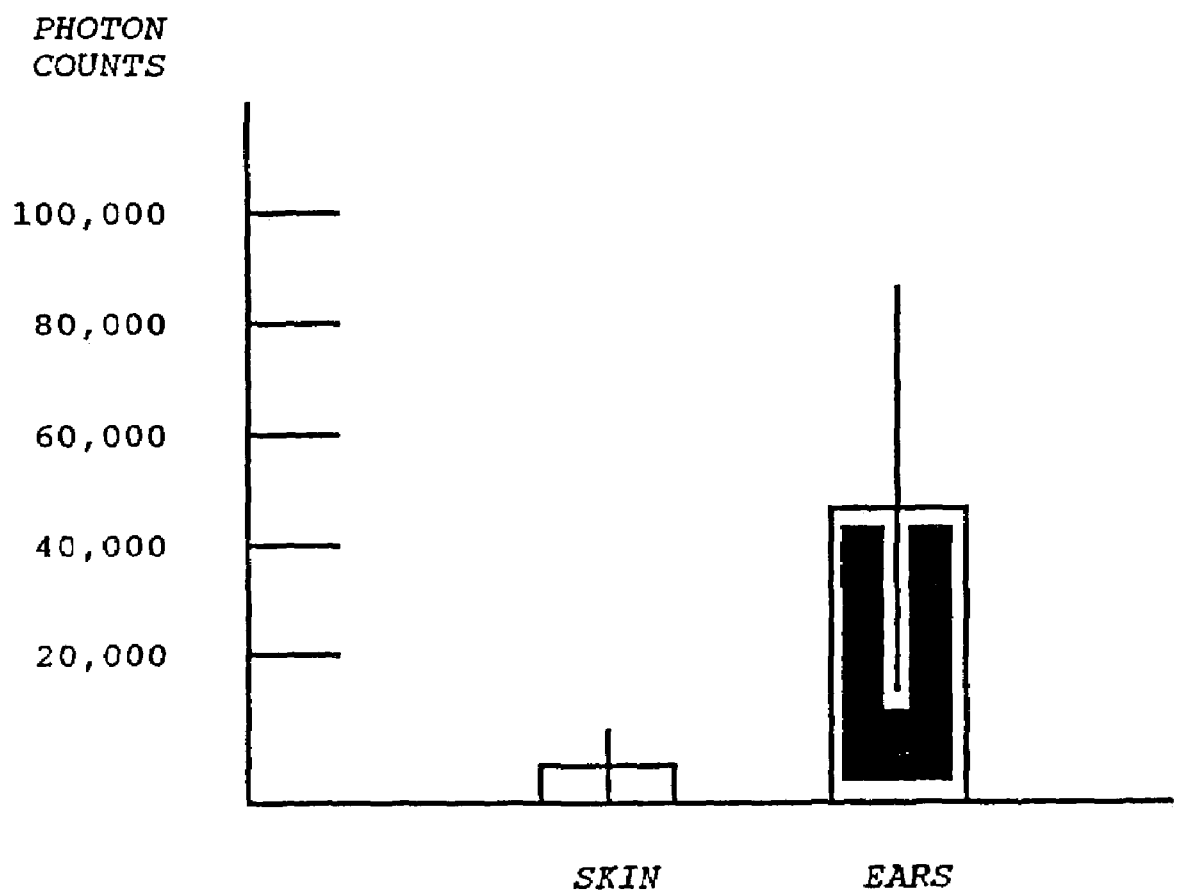

PARTICLE-MEDIATED TRANSFORMATION OF VERTEBRATE TISSUE CELLS

The present application is a Rule 53(b) continuation of U.S. patent application Ser. No. 09/755,199, filed Jan. 8, 2001, now abandoned, which is a continuation of U.S. patent application Ser. No. 08/892,351, filed Jul. 14, 1997, now abandoned, which is a continuation of U.S. patent application Ser. No. 08/103,814, filed Aug. 6, 1993, now abandoned, which is a continuation of U.S. patent application Ser. No. 07/864,638, filed Apr. 7, 1992, now abandoned, which is a division of U.S. patent application Ser. No. 07/437,848, filed Nov. 16, 1989, now abandoned, each of which applications is their entireties are herby incorporated herein by reference. Priority pursuant to 35 U.S.C. § 120 is claimed from all of the foregoing applications.

SUMMARY OF THE INVENTION

This invention relates to the transformation of animal cells and tissue with heterologous DNA by microprojectile bombardment.

BACKGROUND OF THE INVENTION

The transformation of living cells by propelling microprojectiles at those cells at high velocity, with the microprojectiles carrying exogenous DNA or RNA, was originally proposed by T. Klein, E. Wolf, R. Wu and J. Sanford, *Nature* 327, 70 (1987). See also J. Sanford et al., *Particulate Science and Technology* 5, 27 (1987). The original work involved the transformation of onion epidermal cells with RNA derived from tobacco mosaic virus. The findings with onion epidermal cells have been extended to other plants. For example, the transformation of soybean callus by particle bombardment is described by P. Christou et al., *Plant Physiol.* 87, 671 (1988), and the transformation of soybean meristem is described by D. McCabe et al., *Bio/Technology* 6, 923 (1988). See also B. Spalding, *Chemical Week*, 16 (Aug. 31, 1988); European Patent Application Publication No. 0 301 749 to P. Christou et al. The transformation of embryonic maize cells by particle bombardment is described by T. Klein et al., *Proc. Natl. Acad. Sci. USA* 85, 4305 (1988), and the production of transformed maize seed by the particle bombardment of maize pollen is described in European Patent Application Publication No. 0 270 356 to D. McCabe et al.

In addition to the transformation of plants, microprojectile bombardment has been used to transform cellular organelles. Mitochondrial transformation in yeast by particle bombardment is described by S. Johnston et al., *Science* 240, 1538 (1988), and chloroplast transformation in *Chlamydomonas* by particle bombardment is described by J. Boynton et al., *Science* 240, 1534 (1988).

The use of particle bombardment for the transformation of animal tissue or cells has received comparatively little attention. Sanford et al., *Particulate Science and Technology* 5, 27, 35-36 (1987), suggest the use of particle bombardment for human gene therapy, but do not suggest the tissue type or the developmental stage of tissue useful for carrying out such therapy. U.S. patent application Ser. No. 06/877,619, titled "Method for Transporting Substances Into Living Cells and Tissues and Apparatus Therefor," concerns the introduction of biological materials into cells by microprojectile bombardment. Suggested biological substances are stains such as fluorescent or radiolabeled probes, viruses, organelles, vesicles, proteins such as enzymes or hormones, and nucleic acids such as DNA and RNA. Suggested procedures include: (a) the particle bombardment of animal cells such as eggs, bone marrow cells, muscle cells, and epidermal cells at page 16, lines 5-6; (b) the particle bombardment of human tissue or other animal tissue such as epidermal tissue, organ tissue, and tumor tissue at page 16, lines 13-14; and (c) human gene therapy for sickle cell anemia by the particle-mediated transformation of bone marrow tissue at page 22, lines 8-9.

W. Brill, *Particle Propulsion by Electric Discharge* (Tape of Speech at AAAS meeting on Plant Molecular Biology/Genetic Engineering for Agriculture (VI) (January 1989), discusses the transformation of nematodes to correct a missing body wall myosin gene by particle bombardment. The utility of transforming nematodes is, however, comparatively limited.

In view of the foregoing, an object of this invention is to provide new uses for the treatment of animals, particularly vertebrates, and their tissues and cells, by microprojectile bombardment.

A more particular object of this invention is to use microprojectile bombardment as a means for administering proteins or peptides to an animal subject.

SUMMARY OF THE INVENTION

A first aspect of the present invention is a method of transferring a gene to preselected vertebrate cells. The method comprises the steps of, first, providing microprojectiles, the microprojectiles carrying polynucleic acid sequences, the sequences comprising, in the 5' to 3' direction, a regulatory sequence operable in the vertebrate cells and a heterologous gene positioned downstream of the regulatory sequence and under the transcriptional control thereof. The microprojectiles are then accelerated at the preselected cells, with the microprojectiles contacting the cells at a speed sufficient to penetrate the cells and deposit the polynucleic acid sequences therein (as used herein, the plural form of terms such as "cell," "microparticle," and "polynucleic acid sequence" is intended to encompass the singular).

A second aspect of the present invention is a method of transferring a gene to preselected vertebrate tissue. The method comprises the steps of, first, providing microprojectiles, the microprojectiles carrying polynucleic acid sequences, the sequences comprising, in the 5' to 3' direction, a regulatory sequence operable in the vertebrate tissue and a heterologous gene positioned downstream of the regulatory sequence and under the transcriptional control thereof. The microprojectiles are then accelerated at the preselected tissue, with the microprojectiles contacting the cells of the tissue at a speed sufficient to penetrate the cells and deposit the polynucleic acid sequences therein.

A third aspect of the present invention is a method of transferring a gene to a preselected tissue in situ in a vertebrate subject. The method comprises the steps of, first, providing microprojectiles, the microprojectiles carrying polynucleic acid sequences, the sequences comprising, in the 5' to 3' direction, a regulatory sequence operable in the vertebrate tissue and a heterologous gene positioned downstream of the regulatory sequence and under the transcriptional control thereof. The microprojectiles are then accelerated at the animal subject, with the subject positioned so that the microprojectiles contact the preselected tissue, with the microprojectiles contacting the cells of the tissue at a speed sufficient to penetrate the cells and deposit the polynucleic acid sequences therein.

The data disclosed herein provide the first demonstration of particle-mediated transformation of (a) vertebrate cells, (b) vertebrate tissue, and (c) vertebrate tissue in situ of which these applicants are aware.

Also disclosed herein is a method of administering a protein or peptide to a vertebrate subject. This method is based in part on our finding that vertebrate tissue transformed by particle bombardment is surprisingly free of callus formation, inflammation, and other defensive responses. Thus, proteins and peptides released from the transformed cells (by virtue of their being transformed) can circulate throughout the animal subject in which the cells reside, and cells which circulate in the animal subject (e.g., lymphocytes) have access to the transformed cells. In this method, target vertebrate tissue (preferably dermis or hypodermis tissue) is selected and microprojectiles provided. The microprojectiles carry polynucleic acid sequences, the sequences comprising, in the 5' to 3' direction, a regulatory sequence operable in the selected tissue and a gene positioned downstream of the regulatory sequence and under the transcriptional control thereof. The gene codes for a protein or peptide. The microprojectiles are then accelerated at the selected target tissue, with the microprojectiles contacting the cells of the tissue at a speed sufficient to penetrate the tissue cells and deposit the polynucleic acid sequences therein to provide transformed tissue cells. The transformed tissue cells are then maintained in the animal subject, with the transformed tissue cells present in the subject in a number sufficient to produce a physiological response (e.g., an endocrine response, an immune response) to the protein or peptide coded for by the gene in the subject upon expression of the gene.

BRIEF DESCRIPTION OF THE DRAWINGS

The present invention is explained in greater detail in the Examples, Detailed Description, and Figures herein, in which:

FIG. 7 shows peak luciferase activity of skin and ear one day after transfection by microprojectile bombardment.

DETAILED DESCRIPTION OF THE INVENTION

Figure 1:
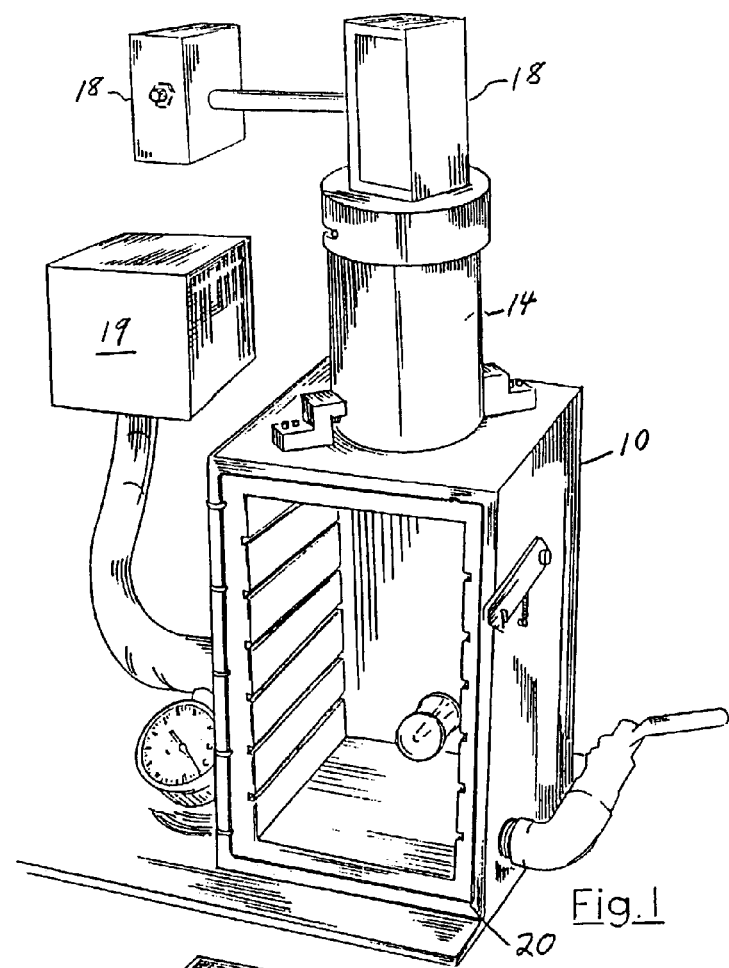
FIG. 1 is a perspective view of a currently available microprojectile bombardment apparatus.
Figure 2:
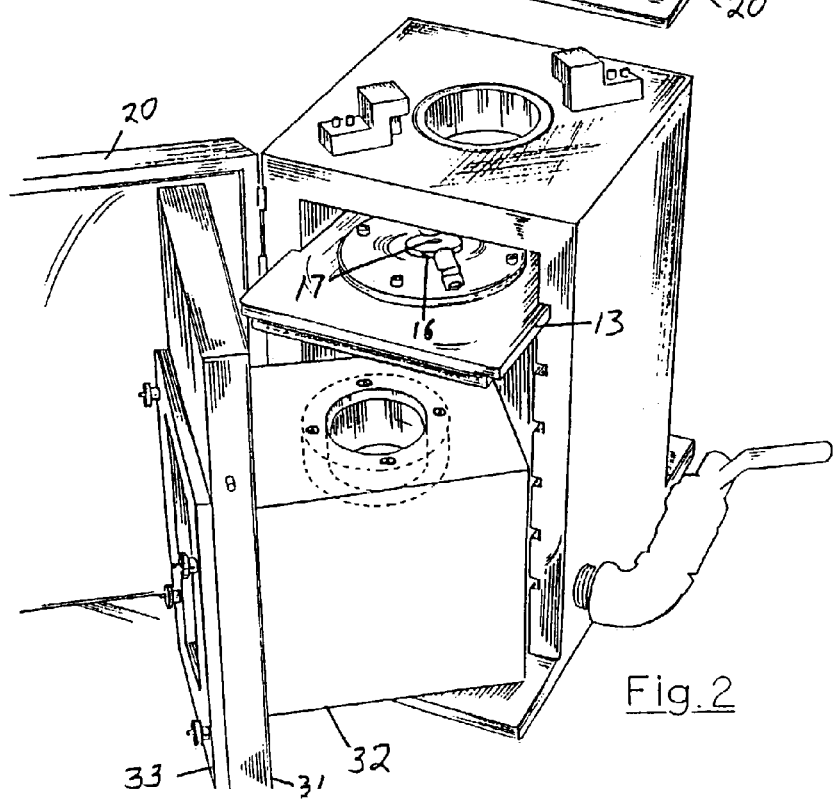
FIG. 2 is a detailed view of the bombardment chamber shown in FIG. 1, with the stopping plate and animal chamber positioned for insertion.
Figure 3:
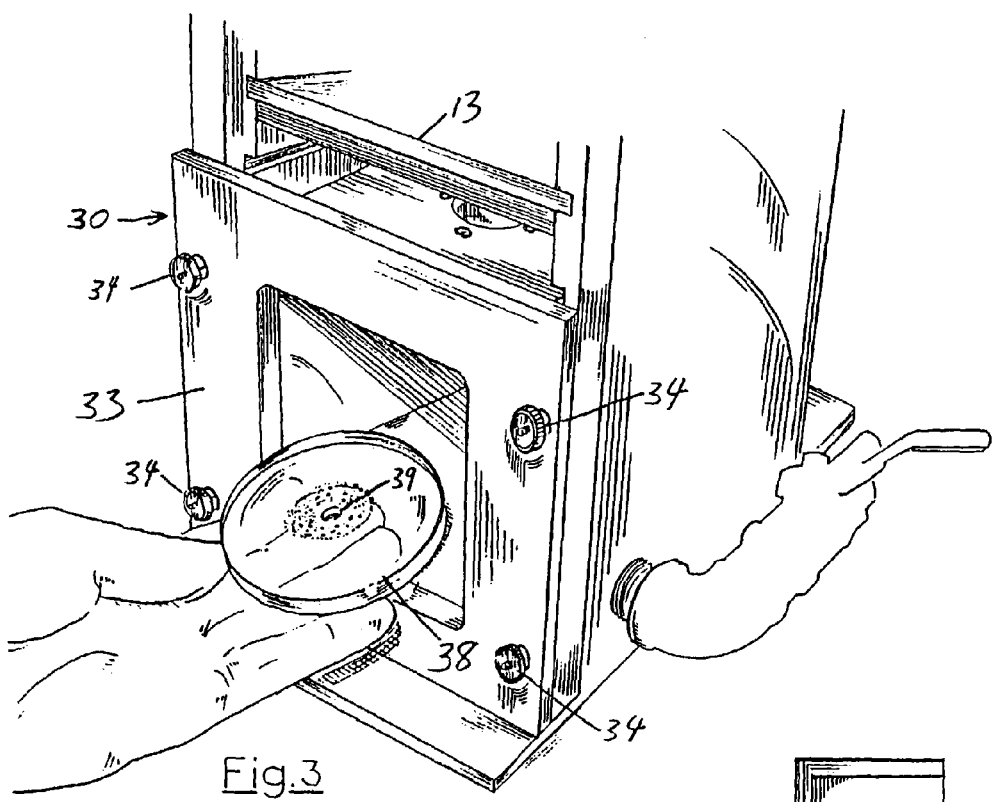
FIG. 3 is a perspective view of an animal chamber positioned in a bombardment chamber, with the animal chamber sealing plate positioned for insertion.
Figure 5:
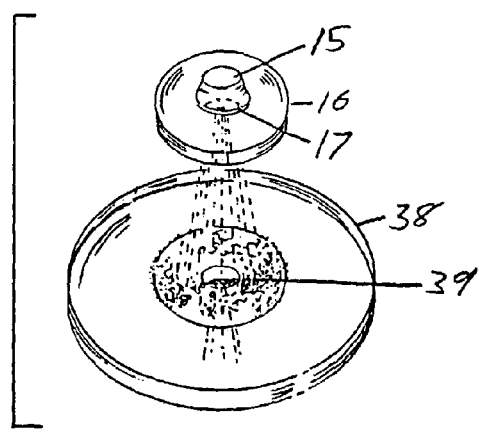
FIG. 5 is a detailed view of a stopping plate and sealing plate, showing the macroprojectile after impact on the sealing plate and the path of travel of the microprojectiles to the sealing plate.
Figure 4:
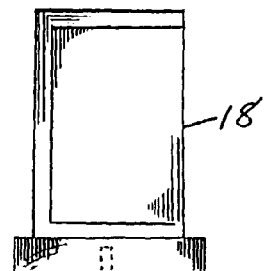
FIG. 4 is a side sectional view of the apparatus shown in FIG. 3, and showing the paths of travel of the macroprojectile to the stopping plate and the microprojectiles from the stopping plate to the subject.
Figure 4:
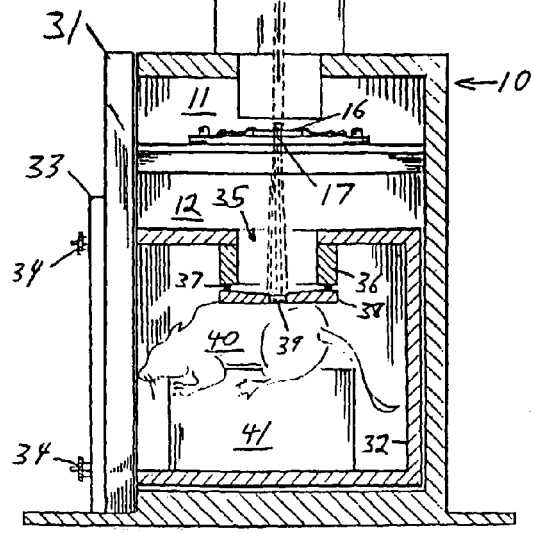

As used herein, the term "tissue" means an aggregation of similarly specialized cells united in the performance of a particular function. The term "tissue cells" means cells residing in a tissue. The term "cell" means a cell either residing in a tissue (i.e., "in situ") or removed from its tissue of origin (i.e., "in vitro").

Animal tissue cells can be bombarded in situ with respect to their tissue of origin, or separated from the tissue and bombarded in vitro. The cells are preferably transformed in situ with respect to the tissue of origin. Tissue to be transformed can likewise be bombarded either in vitro or in situ with respect to the animal of origin or the animal in which the transformed tissue is to subsequently be maintained, depending on the result sought. Preferably, the tissue is transformed in situ in the animal in which it is to be maintained.

Animal subjects to be treated by the method of the present invention are vertebrates, exemplary being fish, reptiles, amphibians, birds, and mammals. Birds (e.g., chicken, turkey) and mammals are preferred, and mammals (e.g., horse, cow, sheep, pig, human) are most preferred. Vertebrate tissues and cells to be treated by the method of the present invention are of corresponding origin, with the origins of the preferred and most preferred tissues and cells corresponding to the preferred and most preferred animals.

The present invention may be practiced on any vertebrate cell, subject to the proviso that cells which have been immortalized in cell culture or otherwise altered from their native state are excluded. Thus, cells to be transformed in the present invention are cells in their naturally occurring state (i.e., primary cells), whether they reside in a tissue or exist free from a tissue in vitro. Cells which have been maintained in vitro for a time sufficient and/or under conditions effective to cause them to lose the characteristics they possess in situ are excluded from the group of cells with which the present invention is concerned.

Vertebrate cells to be treated by the method of the present invention are preferably differentiated cells, and most preferably terminally differentiated cells such as skin cells, hypodermis cells, muscle cells, nerve cells, pancreas cells, and liver cells. Exemplary skin cells include the basal cells and the cells of the dermis and hypodermis.

Vertebrate tissue to be treated by the method of the present invention is likewise preferably differentiated tissue, and most preferably terminally differentiated tissue such as skin tissue, hypodermis tissue, muscle tissue, nerve tissue, pancreas tissue, and liver tissue. Exemplary skin tissues include the basal cell layer, the dermis, and the hypodermis.

The polynucleic acid sequence carried by the microprojectile is a recombinant construct of a gene and a regulatory element. The construct may take any suitable form, such as a plasmid, a genomic viral DNA sequence such as a bovine papillomavirus vector, see E. Chen et al., 299 Nature 529 (1982), a retroviral RNA sequence, derivatives of the foregoing, and synthetic oligonucleotides. The DNA constructs, particularly the plasmids, are currently preferred. Preferred genes which may be used in the polynucleic acid sequence are those which code for a protein or peptide which produces a physiological response (preferably an endocrine response or an immune response) in the animal subject. The gene may be homologous or heterologous with respect to the animal to be transformed, or may be a modified version of a homologous gene.

Exemplary of genes which code for proteins or peptides which produce an endocrine response (i.e., a physiological response in the animal at a point sufficiently removed from the transformed tissue region to require that the protein or peptide travel through the circulatory or lymphatic system of the subject) are genes which code for Factor VIII:C, genes which code for plasminogen activators such as Tissue Plasminogen Activator and urokinase, see, e.g., U.S. Pat. Nos.

4,370,417 and 4,558,010, genes which code for growth hormones such as human or bovine growth hormone, genes which code for insulin, and genes which code for releasing factors such as Luteinizing Hormone Releasing Hormone. The disclosures of all references cited herein are to be incorporated herein by reference.

Exemplary of genes which code for proteins or peptides which produce an immune response (i.e., a response in which B and/or T lymphocytes activated by the protein or peptide are capable of traveling in the circulatory or lymphatic system of the subject to a site removed from the transformed tissue) are genes coding for subunit vaccines such as disclosed in U.S. Pat. No. 4,857,634 to Minor et al. titled "Peptides Useful in Vaccination against Enteroviruses," U.S. Pat. No. 4,738,846 to Rose et al. titled "Vaccine for Vesicular Stomatitis Virus," U.S. Pat. No. 4,428,941 to Galibert et al. titled "Nucleotidic Sequence Coding the Surface Antigen of the Hepatitis B Virus, Vector Containing Said Nucleotidic Sequence, Process Allowing the Obtention Thereof and Antigen Obtained Thereby," and U.S. Pat. No. 4,761,372 to Maas et al. titled "Mutant Enterotoxin of *E. coli*."

An advantage of administering a protein or peptide capable of producing an immune response in the manner described herein is the ability to cause the immunogen to be effectively presented to the subject over an extended period of time. This is in contrast to the simple injection of a protein or peptide, which tend to be rapidly digested and cleared by the subject.

Exemplary of other genes which code for proteins or peptides which produce a physiological response in the subject include genes coding for enzymes such as $\alpha_1$ antitrypsin, genes which code for receptors such as the insulin receptor, see U.S. Pat. No. 4,761,371 to Bell et al., genes which code for adhesons such as the CD4 receptor, see EPO Patent Application Publication No. 0 314 317 of Genentech, titled "Adheson variants, nucleic acid encoding them and compositions comprising them," which may have therapeutic activity in the subject, genes which code for proteins or peptides which will either affect neighboring tissue cells (a paracrine-like action) or will be secreted and affect the secreting cell (an autocrine-like action), and genes which code for pathogen-derived resistance. See J. Sanford and S. Johnston, 113 J. Theor. Biol. 395 (1985); J. Sanford, 130 J. Theor. Biol. 469 (1988).

The polynucleic acid sequence includes a regulatory sequence upstream from, or 5' to, the gene. The regulatory sequence is positioned in the polynucleic acid sequence in operative association with the gene so as to be capable of inducing transcription of the gene. Regulatory sequences which may be used to provide transcriptional control of the gene in the polynucleic acid sequence are generally promoters which are operable in the target tissue cells. Exemplary promoters include, for example, the human α-actin promoter, see T. Miwa and L. Kedes, 7 *Molec. Cell Biol.* 2803 (1987), the human β-actin promoter, J. Leavitt et al., 4 *Molec. Cell Biol.* 1961 (1984), the troponin T gene promoter, see T. Cooper and C. Ordahl, 260 *J. Biol. Chem.* 11140 (1985), the human heat shock protein (HSP) 70 promoter, retrovirus long terminal repeats such as the Rous Sarcoma Virus long terminal repeat, see generally RNA Tumor Viruses (R. Weiss, N. Teich, H. Varmus and J. Coffin Eds. 2d ed. 1984), and the metallothionin gene promoter. The promoter and gene should be capable of operating in the cells, or cells of the tissue, to be transformed (i.e., the promoter should be capable of inducing transcription of the gene, and the gene should code for an mRNA sequence capable of being translated), with the requirements for operability known in the art. See generally R. Old and S. Primrose, Principles of Gene Manipulation (3d Ed. 1985). With respect to tissue, these elements need only be operable in one cell type in that tissue.

Other regulatory elements which may optionally be incorporated into the polynucleic acid sequence include enhancers, termination sequences, and polyadenylation sites, as known in the art, as necessary to obtain the desired degree of expression of the gene in the cell into which it is inserted.

Any microprojectile acceleration cell transformation apparatus can be used in practicing the present invention, so long as the apparatus is modified as necessary for the treatment of air-breathing animals. Exemplary apparatus is disclosed in Sanford et al., *Delivery of Substances into Cells and Tissues using a Particle Bombardment Process,* 5 Particulate Science and Technology 27 (1988), in Klein et al., *High-Velocity Microprojectiles for Delivering Nucleic Acids into Living Cells,* 327 Nature 70 (1987), and in Agracetus European Patent Application Publication No. 0 270 356, titled Pollen-Mediated Plant transformation. We used a commercially available device from Biolistics, Inc., 108 Langmuir Laboratory, Cornell Business and Technology Park, Brown Road, Ithaca, N.Y., 14850. This device is designated a Model BPG-4 Particle Acceleration, Apparatus and is configured essentially as described in Klein et al., 327 Nature 70 (1987). The device, illustrated in FIGS. 1 through 5 (with improvements shown in FIGS. 2-5), comprises a bombardment chamber 10 which is divided into two separate compartments 11,12 by an adjustable-height stopping plate support 13. An acceleration tube 14 is mounted on top of the bombardment chamber. A macroprojectile 15 is propelled down the acceleration tube at stopping plate 16 by a gunpowder charge. A conventional firing mechanism 18 and evacuating apparatus 19 are provided. The stopping plate 16 has a bore hole 17 formed therein which is smaller in diameter than the macroprojectile, the macroprojectile carries the microprojectiles, and the macroprojectile is aimed and fired at the bore hole 17. When the macroprojectile 15 is stopped by the stopping plate 16, the microprojectiles are propelled through the bore hole 17. The target tissue 40, here schematically illustrated as an animal subject, is positioned in the bombardment chamber so that microprojectiles propelled through the bore hole 17 penetrate the cell membranes of the cells in the target tissue and deposit DNA constructs carried thereon in the cells of the target tissue. The bombardment chamber 10 is partially evacuated prior to use to prevent atmospheric drag from unduly slowing the microprojectiles. The chamber is only partially evacuated so that the target tissue is not unduly desiccated during bombardment thereof. A vacuum of between about 20 to 26 inches of mercury is suitable.

Microprojectiles (i.e., microparticles) used in carrying out the present invention may be formed from any material having sufficient density and cohesiveness to be propelled into the cells of the tissue being transformed, given the particle's velocity and the distance the particle must travel. Non-limiting examples of materials for making microprojectiles include metal, glass, silica, ice, polyethylene, polypropylene, polycarbonate, and carbon compounds (e.g., graphite, diamond). Metallic particles are currently preferred. Non-limiting examples of suitable metals include tungsten, gold, and iridium. The particles should be of a size sufficiently small to avoid excessive disruption of the cells they contact in the target tissue, and sufficiently large to provide the inertia required to penetrate to the cell of interest in the target tissue.

Gold particles ranging in diameter from about one micrometer to about three micrometers are preferred for in situ bombardment, and (more particularly) tungsten particles about one micrometer in diameter are preferred for in vitro bombardment of muscle.

The polynucleic acid sequence may be immobilized on the particle by precipitation. The precise precipitation parameters employed will vary depending upon factors such as the particle acceleration procedure employed, as is known in the art. The carrier particles may optionally be coated with an encapsulating agent such as polylysine to improve the stability of polynucleic acid constructs immobilized thereon, as discussed in EPO Application 0 270 356, at Column 8.

Skin in vertebrates is formed from an outer epidermis and an underlying dermis (or corneum). Further underlying the dermis there usually is a loose, spongy layer called the hypodermis which is herein treated by definition as a part of the skin. The dermis and/or the hypodermis are the preferred tissue targets when the object of the transformation is to administer a protein or peptide to the animal subject in a manner which will evoke a physiological response thereto in the animal subject, as discussed above.

In land-dwelling vertebrates such as land-dwelling amphibians, reptiles, birds, and mammals, the epidermis is generally comprised of, from the outer surface to the inner surface, the following layers; (a) the stratum corneum, or horny layer, composed of thin squamous (flat) keratinized cells that are dead and continually being shed and replaced; (b) the stratum lucidum, or clear layer, in which keratinocytes are closely packed and clear, and in which the nuclei are absent and the cell outlines indistinct; (c) the stratum granulosum, or granular cell layer, where the process of keratinization begins; (d) the stratum spinosum, or prickle cell layer, where cells are rich in ribonucleic acid and thereby equipped to initiate protein synthesis for keratinization; and (e) the stratum basale, or basal cell layer, which is composed of a single layer of columnar cells that are the only cells in the epidermis that undergo mitosis. See generally G. Thibodeau, *Anatomy and Physiology*, 114-19 (1987); R. Frandson, *Anatomy and Physiology of Farm Animals*, 205-12 (2d Ed. 1981); R. Nickel et al., *Anatomy of the Domestic Birds*, 156-57 (1977).

The dermis, also called the "true skin," is generally composed of a stratum superficiale, or papillary layer, which immediately underlies the epidermis, and an underlying stratum profundum, or reticular layer. The arteries, veins, capillaries, and lymphatics of the skin are concentrated in the dermis. The reticular layer generally includes a dense network of interlacing white collagenous fibers, skeletal muscles, and involuntary muscles. The papillary layer is composed of loose connective tissue and a fine network of thin collagenous and elastic fibers.

The hypodermis, or superficial fascia, is a loose, spongy subcutaneous layer rich in fat, areolar tissue, and blood vessels. When skin is removed from an animal by blunt dissection, separation usually occurs in the cleavage plane that exists between the hypodermis and underlying tissues, with at least portions of the hypodermis thus adhering to the skin.

In the method of the present invention, dermis and epidermis may be transformed by either (a) propelling the microprojectiles through the epidermis, or (b) surgically exposing the hypodermis and dermis by incision and blunt dissection of a skin flap from the animal and propelling the microprojectiles directly into the hypodermis and dermis without projecting the microprojectiles through the outer surface layer, and then restoring the dissected skin flap to the position oh the animal from which it came. The skin flap can remain attached to the animal for microprojectile bombardment or briefly removed for microprojectile bombardment and then grafted back to the animal. If removed from the animal the skin flap can be returned to the same or a different site on the animal, or can be transplanted to a different animal. We prefer to leave the skin flap attached. We have found greater transformation of the dermis by surgically exposing the dermis so that the microparticles need not pass through the epidermis, but have also found substantial transformation of the dermis even when the microparticles are propelled through the epidermis of land-dwelling vertebrates.

Various aspects of the present invention are explained in the examples which follow. These examples are given to illustrate the invention, and are not to be construed as limiting thereof.

EXAMPLE 1

Particle-Mediated Transformation of Terminally Differentiated Skeletal Myotubes

This example demonstrates that primary cultures of fully differentiated, non-dividing skeletal myotubes can be transformed in vitro using a DNA-particle accelerator. The introduced genes are not rapidly degraded, but remain transcriptionally active over the life of the culture (twelve days).

Myoblast cultures ($4 \times 10^5$ cells) were established from breast muscles of eleven-day chick embryos in gelatin-coated 60 mm plastic dishes in Dulbecco's Minimum Essential Medium (DMEM) supplemented with 10% horse serum and 5% embryo extract. After five days without fresh media, cultures consisted almost entirely of multinucleated myotubes, some of which showed cross-striations. Some cultures were also treated with cytosine arabinoside (ara-C: 1.5 to 3.0 µg/ml) to inhibit growth of residual undifferentiated myoblasts or non-myogenic cells. See G. Paulath et al., *Nature* 337, 570 (1989). At this stage (five days in culture) the conditioned medium was removed and saved, and the plates were placed in a vacuum chamber. Tungsten microprojectiles (mean diameter 1 µm) were coated with pHb-LUC, a plasmid construct in which the firefly luciferase gene, J. de Wet et al., *Molec. Cell Biol.* 7, 725 (1987), is driven by the human B-actin promoter, J. Leavitt et al., *Molec. Cell Biol.* 4, 1961 (1984), a promoter which has strong constitutive activity in these cells. Each culture was bombarded under vacuum (twenty-nine inches Hg) with 2 µl of microprojectile suspension. The macroprojectile was started 3 cm from the top of the barrel and accelerated with a #1 gunpowder 22 caliber cartridge. The petri dish was placed at the bottom of the chamber. The device used and the methods for coating of the microprojectiles are described in J. Sanford et al., *Particulate Sci. Technol.* 5, 27 (1987) and in T. Klein et al., *Nature* 327, 70 (1987). In the present study, pilot experiments were performed to establish the particle velocity, particle size, particle composition, and cell density that resulted in maximal expression of luciferase activity following bombardment for our particular circumstances. Once these conditions were optimized, the experiments described in Table 1 were performed. Whole cell lysates were prepared from cells two days after bombardment and luciferase activity was measured in a Berthold Biolumat LB9500C luminometer following addition of luciferin in the presence of excess ATP. J. de Wet et al., *Molec. Cell Biol.* 7, 725 (1987). These data are also shown in Table 1.

TABLE 1

Expression of firefly luciferase gene driven by the human
β-actin promoter following transfection by microparticle
bombardment of fully differentiated skeletal myotubes.
Luciferase activity
(peak, light emission/60 mm culture dish)

| | |
|---|---|
| Mock transfection (n = 3) | 14 ± 7 |
| pHB-LUC (n = 6) | 112,164 ± 19,086 |
| pHB-LUC + ara-C (n = 6) | 107,620 ± 19,881 |

Transformation by microprojectiles produced reporter gene activities that were 10-20× higher/plate and 200-400× higher/µg DNA than activities obtained by transformation of myotube cultures by standard calcium phosphate co-precipitation. See C. Chen and H. Okayama, *Molec. Cell Biol.* 7, 2745 (1987).

EXAMPLE 2

Fate Over Time of DNA Introduced in Terminally Differentiated Skeletal Myotubules by Particle Bombardment This Example addressed the fate of the introduced DNA over time by measuring the response of an inducible promoter at varying intervals after bombardment. Myotubes were transformed as described in Example 1 above, but with the firefly luciferase gene under the control of the human HSP70 promoter. See B. Wu et al., *Proc. Nat. Acad. Sci. USA* 83, 629 (1986). On days 2-7 following bombardment, luciferase activity was measured in sister cultures that were either maintained at 37° C. (Control=C) or placed at 45° C. for 90 minutes followed by recovery at 37° C. for three hours (Heat Shock=HS).

Figure 6:
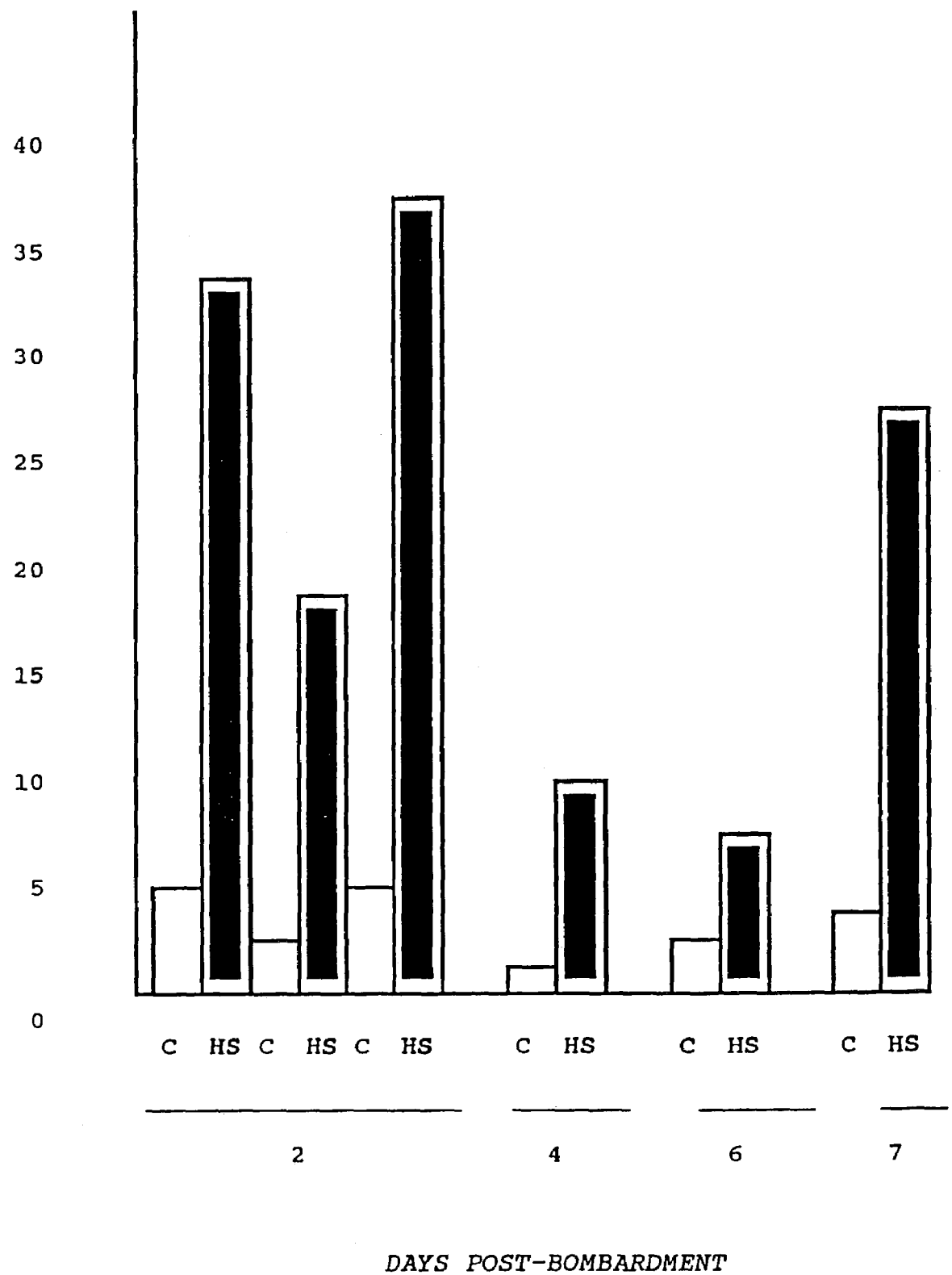
FIG. 6 shows the persistent heat-inducibility of the firefly luciferase gene driven by the human HSP70 promoter after transformation of cultured skeletal myotubes by microprojectile bombardment.

The cultures maintained for 6-7 days following bombardment were re-fed at two day intervals with conditioned media (depleted of mitogenic growth factors) from untransfected myotube cultures. FIG. 6 demonstrates that inducible expression of the introduced plasmid was maintained over this period. As calculated relative to the basal level expression in the control plates, there was no diminution in expression between day 2 (7.9-fold induction) and day 7 (11.9-fold induction) cultures. Thus, there was no substantial degradation of the plasmid or silencing of the heterologous promoter during the lifetime of these cultures.

EXAMPLE 3

Site of Transgene Expression in Cultures of Terminally Differentiated Myotubules This Example was conducted to determine whether transgene expression was occurring within the fully differentiated myotubes, as distinguished from mononuclear cells that remain within these primary cultures. Cultures of differentiated myotubes were transfected, by microprojectile bombardment as described in Example 1, with a plasmid construct containing the Drosbphila Alcohol Dehydrogenase (ADH) gene under the control of the Rous Sarcoma Virus long terminal repeat (pRSV-ADH). On the following day, cells were fixed and stained according to the method described by C. Ordahl et al., *Molecular Biology of Muscle Development* 547 (C. Emerson et al. Eds. 1986), and photographed under phase contrast with misaligned phase rings.

Although Drosophila ADH was detectable in mononuclear cells, the large majority of the activity was found within multinucleated fused myotubes. Interestingly, two patterns of myotube staining were evident. In some myotubes, ADH activity was spatially limited around a single nucleus, while the remainder of the multinucleated cell was devoid of activity. This staining pattern suggests that conditions existed in these cells to restrict expression of the transgene to a spatial domain surrounding an individual nucleus. However, in other myotubes, ADH staining was distributed uniformly throughout the cell. This diffuse pattern of transgene expression implies either that multiple nuclei were transformed in a single myotube, or that, under some conditions, the ADH protein was free to diffuse throughout the entire span of these elongated cells. In view of the apparent frequency of transformation, the latter explanation is favored.

EXAMPLE 4

Transformation of Alternate Cells with pRSV ADH

The experiment described in example 3 above was repeated in essentially the same manner, except that cardiac cells in vitro were used instead of skeletal myotubes. No positive results were seen. The lack of transformation was apparently due to the very few number of cells on the plate of cells used.

The experiment described in example 3 above was again repeated in essentially the same manner, except that whole mouse diaphragm was used instead of skeletal myotubes. The diaphragm was held flat on a dish with a piece of screen and the screen held down by weights. No transformation was seen. It appears that the 1 micron tungsten microparticles employed did not have sufficient kinetic energy to penetrate the diaphragm tissue.

EXAMPLE 5

Apparatus for Transformation of Animals

The device employed in the above examples was modified for the transformation of tissue in whole animals in the manner illustrated in FIGS. 1 through 5. The door 20 on the bombardment chamber 10 was opened and an animal bombardment fitting, 30 or "trap," inserted. The animal bombardment fitting included a cover plate 31 and an animal chamber 32. The animal chamber 32 has a top wall, bottom wall, side walls, a back wall, and an outer flange 33. The chamber 32 is inserted through an opening in the cover plate and sealed thereto by means of a rubber gasket on the front side of the cover plate positioned between the cover plate opening and the edge of the animal chamber flange. Threaded fasteners 34 secure the animal chamber 32 to the cover plate 31. The back side of the cover plate has a rubber gasket spaced inwardly from the outer edge thereof for sealing the cover plate to the bombardment chamber 10.

The top of the animal chamber has an opening 35 formed therein which, when the animal chamber is installed in the bombardment chamber, is axially aligned with the center axis of the bore hole 17 of the stopping plate 16. An inner cylindrical sleeve 36, open at the top and bottom, is connected and sealed in the top opening 35. The bottom edge portion of the inner sleeve has a rubber gasket 37 inserted therein.

A sealing plate 38 is provided for sealing the bottom opening of the inner sleeve 36. The sealing plate has a center opening 39 formed therein. The surface of the tissue on the animal subject 40 to be transformed is placed in contact with the sealing plate 38 so that the tissue to be transformed is accessible through the center opening 39. The sealing plate 39 is then placed in contact with the bottom edge portion of the inner sleeve 36 and a vacuum drawn in the vacuum chamber. The contact of the subject tissue to the sealing plate 38, the sealing plate to the inner sleeve 36, the inner sleeve to the animal chamber 32, the animal chamber to the cover plate 31 and the cover plate to the bombardment chamber 10 all operate to seal the bombardment chamber 10. A screen is provided across the center opening of the sealing plate on the bottom surface thereof to reduce the tendency of tissue to be drawn into the chamber. When the microprojectiles are accelerated, the opening 39 in the sealing plate 38 is positioned so that the microprojectiles contact the tissue surface accessible through the opening. A sponge or other spacing means 41 can be used to hold the animal subject up against the sealing plate.

EXAMPLE 6

Particle Bombardment of Euthanized Mice

Mice were euthanized and the hair removed from their hind legs with a depilatory (NEET™) to expose the skin on the hind legs. The skin was then either left in position or dissected away to expose underlying muscle. The animals were positioned in the apparatus described in example 5 above, either hind leg skin or muscle tissue positioned for bombardment, a vacuum of 26 inches of mercury drawn in the chamber, and the tissue bombarded with 1 micron tungsten microprojectiles. 1 micron tungsten particles were found too small to penetrate either muscle or skin. 3.4 micron tungsten particles were then tried, and were found to penetrate muscle and skin. Best were gold particles, 1 to 3 microns in diameter.

EXAMPLE 7

Particle Bombardment of Skin and Ear in Live Mice

Live adult female Balb C and Charles River CD1 mice were transformed by the apparatus and procedures described in the preceding examples. Gold particles 1 to 3 microns in diameter were coated with pHb-LUC by precipitation, as described above. Animals were anesthetized with a mixture containing equal parts of ketamine and xylazine (0.067·mg/g body weight). The target areas were hind leg skin and ear, which were prepared with a depilatory as described above. A vacuum of 26 inches of mercury was drawn for hind leg skin and 20 inches of mercury drawn for ear. After bombardment, the tissue showed little or no evidence of damage. A faint brown stain was evident in the area containing particles in most animals and, rarely, a small (<1 mm$^2$) area of intradermal hemorrhage from small blood vessels was noted. Peak luciferase activity of the skin and ears on day one after transfection in counts per minute is shown in FIG. 7. The values are means ± the standard deviation. The activity of 17 skin samples was 4,699±4,126 and the activity of 12 ear samples was 47,114±3,679. Photoluminescence was determined in duplicate on a Berthold LB 9500 C luminometer set for a ten second period of integration with 50 microliter (skin) and 25 microliter (ear) samples of extract. The mean luciferase activity for skin and ear over time in counts per minute is shown in Table 2 below.

TABLE 2

Luciferase Activities for Days 1 to 4

| | | DAY: | | | |
|---|---|---|---|---|---|
| | | 1 | 2 | 3 | 4 |
| Skin: | mean | 4699 | 810 | 217 | 104 |
| | s.d. | 4126 | 1097 | 265 | 140 |
| Ear: | mean | 149369 | 116114 | 69986 | |
| | s.d. | 49392 | 122455 | 66461 | |

After recovery from anesthesia, animals showed no behavioral abnormalities and did not manifest evidence of pain or itching in the transformed area of skin. Histologic examination of bombarded skin revealed no significant alteration of tissue structure, and only occasional lymphocytes or polymorphonuclear leukocytes within the transformed area. In situ hybridization studies revealed a high proportion (approximately 25%) of cells within the epidermis that expressed luciferase mRNA, and a lower (but noticeable) proportion in the dermis had hair follicles.

EXAMPLE 8

Local Transgene Activity in Ear of Live Mice by Particle Bombardment

Mouse ears were transformed with pGH precipitated on 1 to 3 gold microparticles as described in Example 7 above. The plasmid pGH includes a human growth hormone (HGH) gene driven by a metallothionin promoter. Local levels of HGH were measured with a commercially available Nichols Institute Allegro™ HGH Radioimmunoassay. The RIA data is given in Table 3 below. Activity is expressed in counts per minute.

TABLE 3

Local HGH Activity in Mouse Ear

| Group | Activity |
|---|---|
| Positive Control | 441 |
| Left Ear | 520 |
| Right Ear | 220 |
| Negative Control | 90 |
| Negative Control | 67 |

The foregoing examples are illustrative of the present invention, and are not to be taken as limiting thereof. The invention is defined by the following claims, with equivalents of the claims to be included therein.

That which is claimed is:

1. An agent for genetically transforming tissue cells of a living vertebrate, said agent comprising microparticles coated with stabilizing agent and carrying a polynucleotide sequence, said polynucleotide sequence comprising, in the 5' to 3' direction, (1) a regulatory sequence operable in vertebrate tissue; and positioned downstream of said regulatory sequence and under the transcriptional control thereof, (2) a nucleotide sequence encoding a protein or peptide immunogen from a vertebrate pathogen against which an immune response is desired, wherein upon expression of said nucleotide sequence encoding the protein or peptide immunogen in the tissue cells, said vertebrate exhibits an immune response to said protein or peptide immunogen.

2. An agent according to claim 1, wherein the microparticles are metallic.

3. An agent according to claim 1, wherein the microparticles are gold.

4. An agent according to claim 1, wherein the microparticles are a polymer material.

5. An agent according to claim 1, wherein the microparticles are a polymer material selected from the group of polyethylene, polypropylene, and polycarbonate.

6. An agent according to claim 1, wherein the microparticles have diameters of from 1 micron to 3 microns.

7. An agent according to claim 1, wherein the vertebrate tissue is muscle tissue.

8. An agent according to claim 1, wherein the vertebrate tissue is skin tissue.

9. An agent according to claim 1, wherein the skin tissue is selected from the group of dermis tissue and hypodermis tissue.

10. An agent according to claim 1, wherein the vertebrate is a human.

11. An agent according to claim 1, wherein the polynucleotide sequence comprises a further regulatory sequence selected from the group of enhancers, termination sequences, and polyadenylation sites.

12. An agent according to claim 1, wherein the regulatory sequence is operable in only one cell type in the vertebrate tissue.

13. An agent according to claim 1, wherein the nucleotide sequence encoding a protein or peptide immunogen codes for subunit vaccine.

14. An agent according to claim 13, wherein the nucleotide sequence encoding a protein or peptide immunogen codes for the surface antigen of the Hepatitis B virus.

15. An agent according to claim 1, wherein the polynucleotide sequence is immobilized on the microparticles by precipitation.

16. An agent according to claim 1, wherein the microparticles are coated with polylysine.

17. An agent according to claim 1, wherein the vertebrate pathogen is a virus.

* * * * *